US012557978B2

(12) United States Patent
Gu et al.

(10) Patent No.: US 12,557,978 B2
(45) Date of Patent: Feb. 24, 2026

(54) SYSTEM AND METHOD FOR PAIRING MEDICAL DEVICES

(71) Applicant: Covidien LP, Mansfield, MA (US)

(72) Inventors: Jianfeng Gu, Shanghai (CN); Junhua Song, Shanghai (CN); Mingxia Sun, Shanghai (CN); Chunlang Hong, Shanghai (CN)

(73) Assignee: Covidien LP, Mansfield, MA (US)

( * ) Notice: Subject to any disclaimer, the term of this patent is extended or adjusted under 35 U.S.C. 154(b) by 399 days.

(21) Appl. No.: 18/040,120

(22) PCT Filed: Aug. 28, 2020

(86) PCT No.: PCT/CN2020/112053
§ 371 (c)(1),
(2) Date: Jan. 31, 2023

(87) PCT Pub. No.: WO2022/041107
PCT Pub. Date: Mar. 3, 2022

(65) Prior Publication Data
US 2023/0263383 A1     Aug. 24, 2023

(51) Int. Cl.
*A61B 1/267*     (2006.01)
*A61B 1/00*     (2006.01)
*A61B 1/04*     (2006.01)

(52) U.S. Cl.
CPC .......... *A61B 1/267* (2013.01); *A61B 1/00006* (2013.01); *A61B 1/00016* (2013.01); *A61B 1/00059* (2013.01); *A61B 1/04* (2013.01)

(58) Field of Classification Search
None
See application file for complete search history.

(56) References Cited

U.S. PATENT DOCUMENTS 10,307,599 B2     6/2019     Schilling
2008/0029100 A1     2/2008     Glassenberg et al.
(Continued)

FOREIGN PATENT DOCUMENTS

CN     101729084 A     6/2010
CN     103180012 A     6/2013
(Continued)

OTHER PUBLICATIONS

European Search Report for EP Application No. 20950777.1 mailed Apr. 10, 2024 (11 pages).
(Continued)

*Primary Examiner* — Tessa M Matthews

(57)     ABSTRACT

A medical device monitoring system includes a monitor and a medical device. The monitor includes an infrared emitter that transmits a first infrared signal, the first infrared signal comprising identification information of the monitor, a second infrared signal comprising the identification information, and a time gap between the first infrared signal and the second infrared signal and a controller that activates the infrared emitter and that sets the time gap the first infrared signal and the second infrared signal. The monitor communication circuitry. The medical device includes a medical sensor and an infrared receiver disposed on the video laryngoscope and that receives the first infrared signal and the second infrared signal. The medical device also includes communication circuitry that communicates the acquired airway images to the monitor communication circuitry when a processor validates a pairing between the video laryngoscope and the monitor.

20 Claims, 7 Drawing Sheets

(56) References Cited

U.S. PATENT DOCUMENTS

| | | | |
|---|---|---|---|
| 2010/0081875 | A1 | 4/2010 | Fowler et al. |
| 2018/0172664 | A1 | 6/2018 | Love et al. |
| 2019/0133430 | A1* | 5/2019 | Inglis .................. A61B 1/0005 |
| 2019/0290108 | A1* | 9/2019 | Nakamitsu ............... A61B 1/00 |
| 2019/0298952 | A1 | 10/2019 | Taniguchi et al. |
| 2024/0398221 | A1* | 12/2024 | Inglis ................. A61B 1/00016 |

FOREIGN PATENT DOCUMENTS

| | | | | |
|---|---|---|---|---|
| CN | 103891393 | A | | 6/2014 |
| CN | 207055474 | U | | 3/2018 |
| CN | 108969105 | A | | 12/2018 |
| CN | 109414156 | A | | 3/2019 |
| JP | 2010005326 | A | * | 1/2010 |
| WO | 03/009749 | A1 | | 2/2003 |

OTHER PUBLICATIONS

International Written Opinion for International Application No. PCT/CN2020/112053 mailed Apr. 29, 2021 (4 pages).
International Search Report for International Application No. PCT/CN2020/112053 mailed Apr. 29, 2021 (4 pages).
First Office Action for Chinese Patent Application No. 202080103214.5 mailed Nov. 30, 2024, 33 pages.

\* cited by examiner

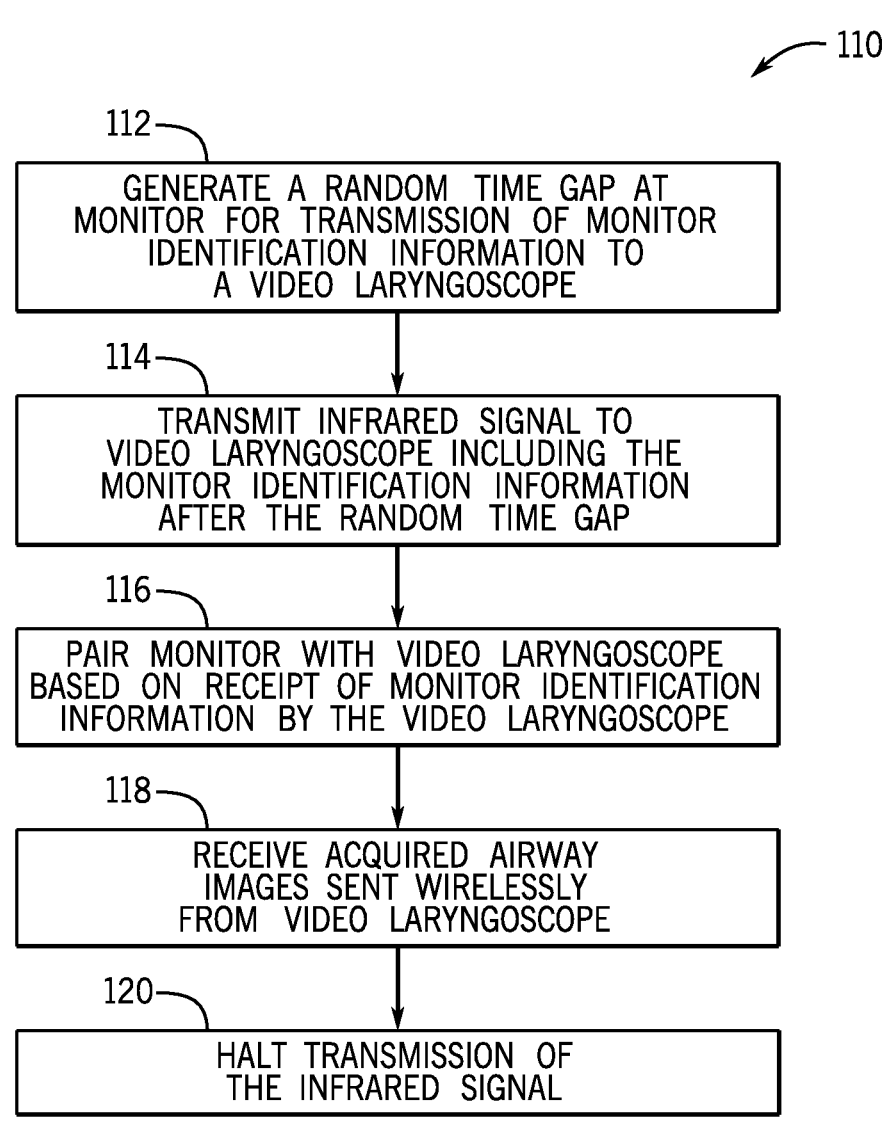

110

112 —
GENERATE A RANDOM TIME GAP AT
MONITOR FOR TRANSMISSION OF MONITOR
IDENTIFICATION INFORMATION TO
A VIDEO LARYNGOSCOPE

114 —
TRANSMIT INFRARED SIGNAL TO
VIDEO LARYNGOSCOPE INCLUDING THE
MONITOR IDENTIFICATION INFORMATION
AFTER THE RANDOM TIME GAP

116 —
PAIR MONITOR WITH VIDEO LARYNGOSCOPE
BASED ON RECEIPT OF MONITOR IDENTIFICATION
INFORMATION BY THE VIDEO LARYNGOSCOPE

118 —
RECEIVE ACQUIRED AIRWAY
IMAGES SENT WIRELESSLY
FROM VIDEO LARYNGOSCOPE

120 —
HALT TRANSMISSION OF
THE INFRARED SIGNAL

FIG. 7

SYSTEM AND METHOD FOR PAIRING MEDICAL DEVICES

CROSS REFERENCE TO RELATED APPLICATIONS

This application is a National Stage Application of PCT/CN2020/112053 filed on Aug. 28, 2020, and which application is incorporated herein by reference. To the extent appropriate, a claim of priority is made to the above disclosed application.

BACKGROUND

The present disclosure relates generally to medical devices and, more particularly, to communication between components of monitoring systems.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of any kind.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients.

Medical devices may include sensors that acquire patient information (e.g., medical data, medical images) and that communicate the patient information to a patient monitor or separate device. While some sensors and monitors are coupled to one another via communication cables, this arrangement may constrain a clinician's movement during a medical procedure. As such, it may be desirable to acquire patient information using wireless sensors that communicate information to a separate monitor or display to enable a clinician to have greater freedom of movement while monitoring is being performed.

Such medical devices that communicate wirelessly are typically paired with a patient monitor to ensure that the patient monitor is displaying physiological information from the intended source. This may be achieved by manually entering device-related information into the patient monitor. However, manual entry is time-consuming, and may not be updated in a timely manner as devices are reused between patients.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a video laryngoscope monitoring system includes a monitor. The monitor includes an infrared emitter that is activated to emit an infrared signal. The infrared signal includes a first signal portion having identification information of the monitor and a second signal portion having the identification information. There is a random time gap, the random time gap based on a random number or a pseudorandom number, between the first signal portion and the second signal portion. The monitor also includes a controller that activates the infrared emitter and that sets the random time gap between the first signal portion and the second signal portion. Further, the monitor includes monitor communication circuitry. The video laryngoscope monitor system also includes a video laryngoscope. The video laryngoscope includes a camera that acquires airway images of a patient. The video laryngoscope also includes an infrared receiver disposed on the video laryngoscope and that receives the infrared signal infrared signal from the infrared emitter having the identification information of the monitor. Further, the video laryngoscope includes communication circuitry that wirelessly communicates with the monitor communication circuitry. Further still, the video laryngoscope includes processor that extracts the identification information from the infrared signal, validates a pairing between the video laryngoscope and the monitor based on the extracted identification information; and instructs the communication circuitry to wirelessly communicate the acquired airway images to the monitor associated with the identification information based on the validated pairing.

In one embodiment, a medical device monitoring system includes a plurality of monitors, and each monitor of the plurality of monitors has an infrared emitter that is activated to emit an infrared signal comprising identification information of a respective monitor. The identification information is repeated in the infrared signal with a random time gap between repeats. Each monitor also has a controller that activates the infrared emitter and that sets the random time gap in the infrared signal of the respective monitor. Further, each monitor includes monitor communication circuitry. The medical device monitoring system also includes a medical device. The medical device includes a sensor that acquires medical device data of a patient. The medical devices also includes an infrared receiver disposed on the medical device and that receives the infrared signal comprising the identification information from each monitor of the plurality of monitors in accordance with the random time gap of each infrared emitter. Further, the medical device includes a processor that extracts the identification information from the infrared signal of each monitor. Further still, the medical device includes communication circuitry that communicates the medical device data to the monitor communication circuitry of at least one monitor of plurality of monitors using the identification information of the at least one monitor extracted from the infrared signal.

In one embodiment, a method includes setting a random time gap based on a signal transfer time of identification information associated with a monitor. The method also includes driving transmission of an infrared signal by an infrared emitter, the infrared signal comprising repeats of the identification information, wherein at least two of the repeats are separated by a signal off period having a length based on the random time gap. Further, the method includes pairing with a medical device based on receipt of the infrared signal by an infrared receiver of the medical device, wherein the pairing comprises extracting the identification information from the infrared signal and validating the identification information. Further still, the method includes receiving medical device data from the medical device based on the pairing.

BRIEF DESCRIPTION OF THE DRAWINGS

Advantages of the disclosed techniques may become apparent upon reading the following detailed description and upon reference to the drawings in which:

FIG. 7 illustrates a flow diagram for pairing and communicating data in the system of FIG. 6, according to an embodiment of the present disclosure.

DETAILED DESCRIPTION OF SPECIFIC EMBODIMENTS

In certain clinical settings, such as in an operating room or when intubating a patient, it may be beneficial to display medical device data obtained by a wireless medical device on a separate monitor, thereby allowing multiple medical professionals to view the medical device data in real time. The wireless medical device may pair with an appropriate monitor via exchanging or receiving identification information from the monitor (or vice versa). The identification information may be used to identify or validate incoming signals between the medical device and the monitor and/or to establish wireless communication permissions or protocols between these devices. The present techniques provide systems and methods of optical communication and pairing between devices, e.g., between medical devices. The disclosed pairing techniques prevent or reduce interference between multiple optically-emitting devices (e.g., infrared emitters) to permit a receiver to receive a clear and resolvable signal that in turn will permit pairing between respective devices associated with the emitter and receiver.

Figure 1:
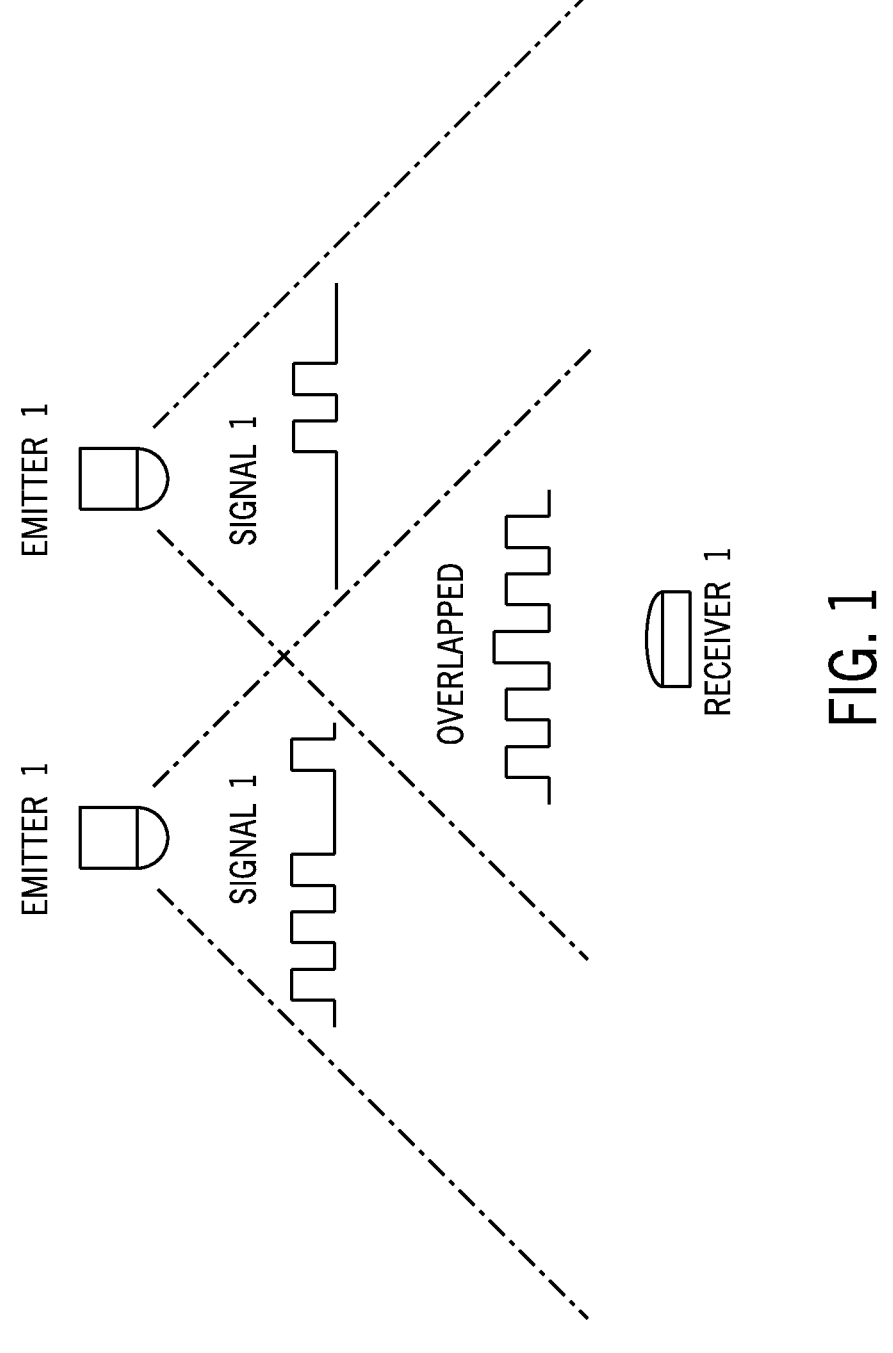
FIG. 1 illustrates a schematic diagram of an emitter and receiver system that exhibits interference between multiple emitters at a receiver.

Infrared remote control or communication uses optical signals transmitted from an infrared emitter and received by an infrared receiver in transmission range of the infrared emitter. While infrared signals cannot generally transmit through walls into adjacent rooms, multiple infrared-emitting devices that operate in the same wavelength band and that are co-located in one room will interfere with one another, preventing infrared receivers in the room from receiving resolvable information. For example, FIG. 1 is a schematic illustration of an environment with multiple emitters, shown here as Emitter 1 and Emitter 2, simultaneously transmitting electromagnetic signals (e.g., Signal 1 and Signal 2, respectively) that are received by any available receiver in range. In the illustrated example, Receiver 1 is in range. The Signal 1 and the Signal 2 interfere, which produces an unresolvable signal that is a combination of the two signals (e.g., Overlapped) as shown in the illustrated embodiment. While Signal 1 and Signal 2 may include identification information that uniquely identifies devices associated with the Emitter 1 and the Emitter 2, respectively, such as a media access control (MAC) address, an IP address, a unique device identifier, and the like, the identification information may be lost in the Overlapped signal. As such, the Receiver 1 cannot identify the information from Emitter 1 and Emitter 2 based on the Overlapped signal between Signal 1 and Signal 2. Therefore, the Receiver 1 cannot pair with Emitter 1 and/or Emitter 2, and thus, cannot communicate information. Accordingly, as illustrated in FIG. 1, simultaneous transmission of optical signals by multiple emitters in an environment may prevent efficient optical pairing via an emitter and a receiver. The disclosed techniques prevent or reduce overlapping between simultaneously transmitted optical signals such that the received signal is more easily resolved, thus improving pairing between devices to permit medical device data (e.g., physiological measurements, medical images) to be displayed.

For example, a disclosed signal time separation technique according to aspects of the disclosure may improve the efficiency of device pairing by reducing incidences of unsuccessful pairing attempts. The disclosed signal time separation techniques introduce a random time gap in transmitted identification information from each emitter. Because a device associated with each emitter sets the time gap (e.g., time delay) randomly and independently, the portion of the transmitted signal that includes the identification information is less likely overlap with signals transmitted by other emitters. That is, each transmitted signal will include a dark period or signal off period of random duration to avoid overlap of the identification information signals between emitters. In an embodiment, the disclosed signal time separation techniques may be implemented on one side of the pairing, e.g., the monitor-side. In this manner, specialty medical devices with custom operating systems that are more complex to alter may not be modified or upgraded, but will nonetheless benefit by receiving more resolvable signals to facilitate pairing.

Figure 2:
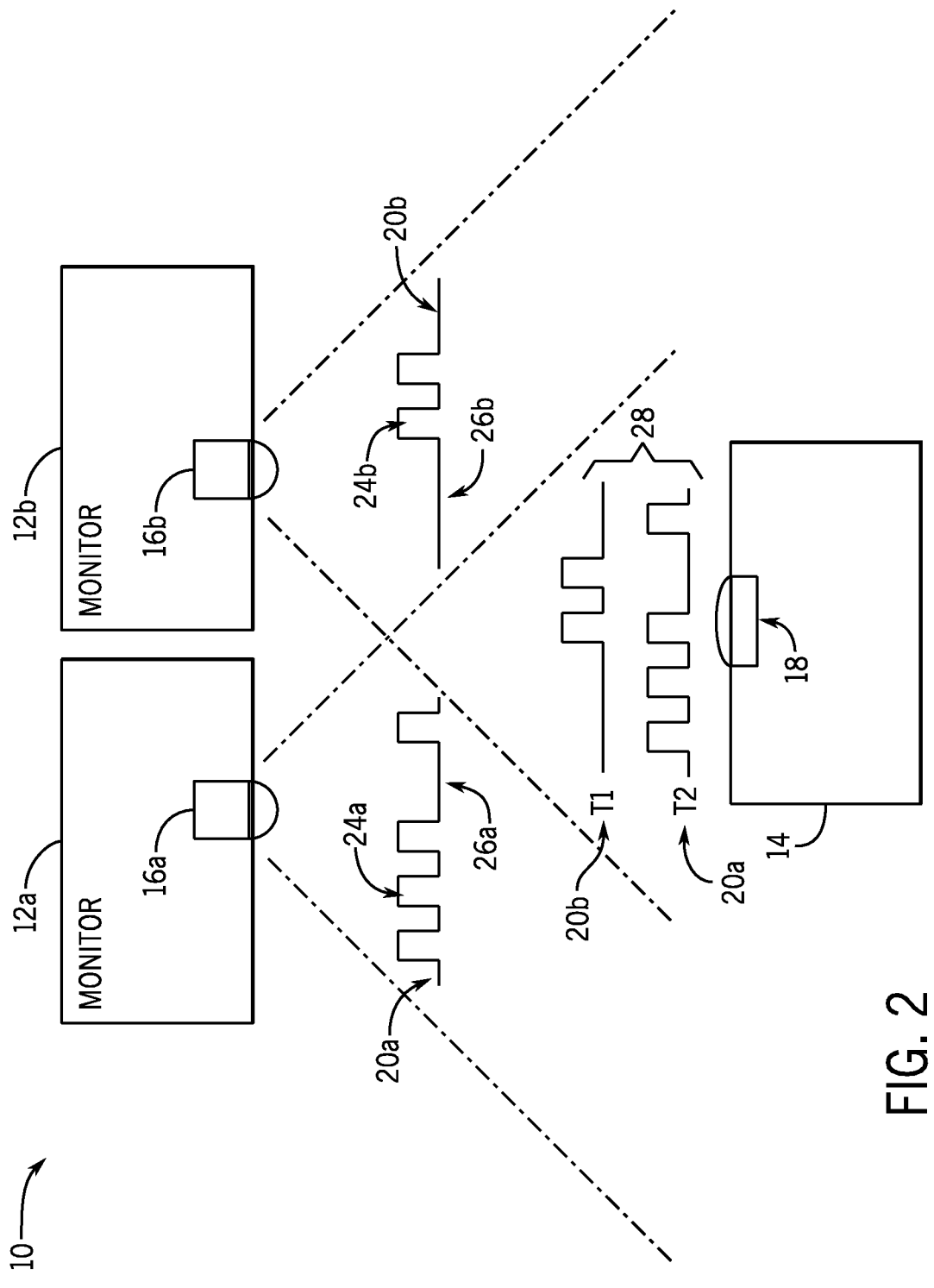
FIG. 2 illustrates a schematic diagram of a medical device monitoring system, according to an embodiment of the present disclosure.

With the foregoing in mind, FIG. 2 is a block diagram of components of a medical device monitoring system 10 that includes multiple monitors 12 and a medical device 14. In general, the monitor 12 is an electronic device having a processor that performs one or more operations such as providing images on a display of the monitor 12, recording data on a memory, or transferring of data to another device (e.g., streaming or automatic transfer at various times). For example, the monitor 12 may include a display that depicts visualizations associated with medical device data captured, measured, acquired, and/or obtained by the medical device 14. The monitor 12 includes an emitter 16 that generally allows the monitor 12 to pair with the medical device 14. More specifically, the emitter 16 may emit, send, or transmit infrared signals that are received by a receiver 18 of the medical device 14 within a suitable range of the monitor. In an embodiment, the infrared signals may be in a range of 700 nm to 1 mm. In one embodiment, the infrared signal is a near infrared signal in a range of 750 nm-1400 nm. While, in embodiments of the disclosure, the emitter 16 is discussed as sending infrared signals, it should be noted that the emitter 16 may be capable of emitting other types of electromagnetic signals within other bands of the electromagnetic spectrum. Further, while certain embodiments show the emitter 16 on the monitor 12 and the receiver on the medical device 14, it should be understood that, additionally or alternatively, these positions may be exchanged.

In general, the medical device 14 is a processor-based device that performs one or more operations such as capturing, measuring, acquiring, and obtaining medical device data. The medical device data refers to data acquired by a medical sensor of the medical device 14. For example, the medical device 14 may be a video laryngoscope that includes a sensor, e.g., a camera. As such, medical device data acquired by the medical device 14 may include airway images of a patient. Additionally or alternatively, the medical device data may include patient images of other regions, physiological parameter data (e.g., oxygen saturation, carbon dioxide measurements, blood pressure data). In an embodiment, the medical device 14 may be a drug delivery device, tool, or surgical instrument that is controlled or operated by the monitor 12.

To prevent or reduce a likelihood of the infrared signal 20a emitted by emitter 16a from interfering with the infrared signal 20b emitted by the emitter 16b, the emitters 16a and 16b may emit their respective infrared signals 20a and 20b to include identification information 24a, 24b separated by a time gap 26a, 26b. By transmitting the infrared signals 20a and 20b with a time gap, the receiver 18 may receive data 28 representative of two resolvable infrared signals 20a and 20b. The infrared signal 20a corresponds to the infrared signal 20a transmitted by the emitter 16a of the monitor 12a, and the infrared signal 20b corresponds to the infrared signal 20b transmitted by the emitter 16b of the monitor 12b.

Figure 3:
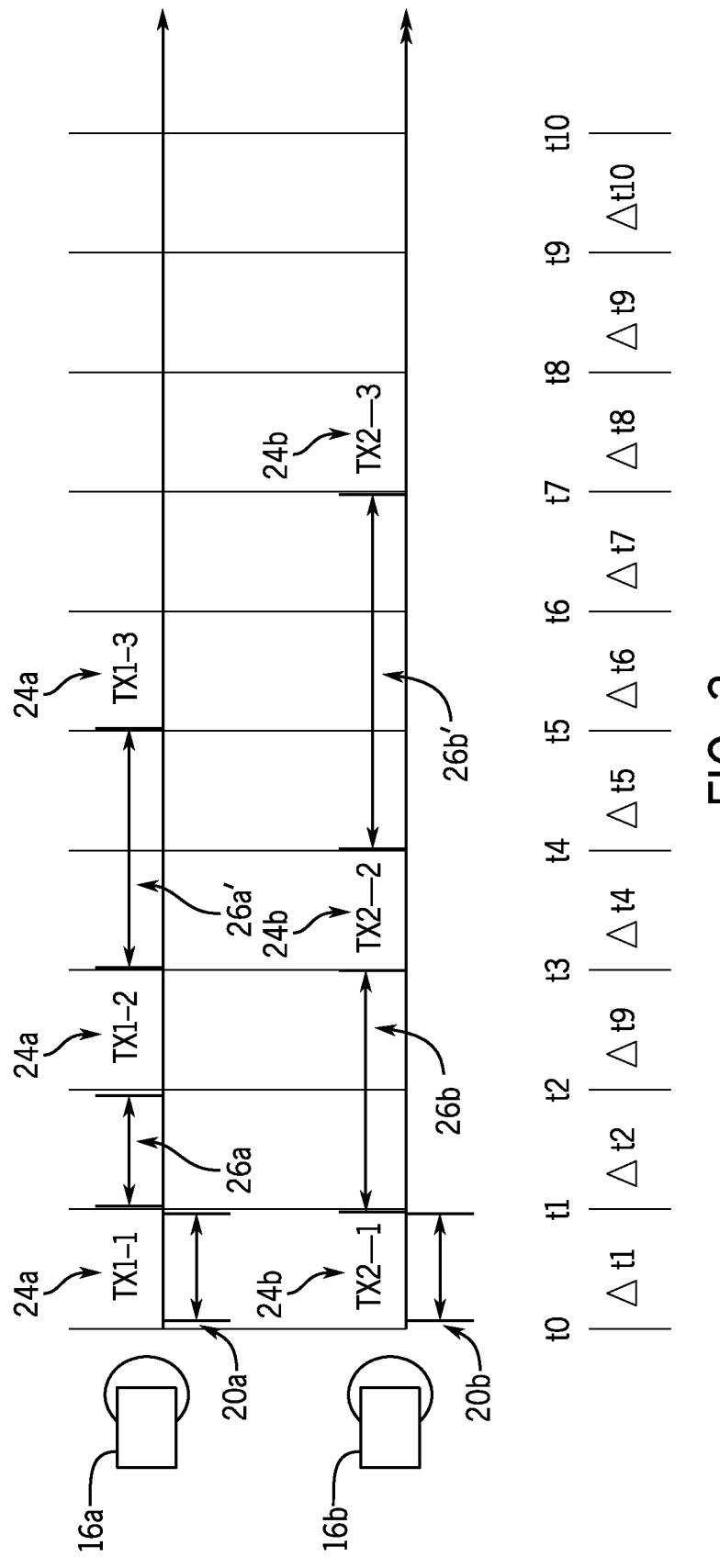
FIG. 3 illustrates a timing diagram of signals emitted with a random time gap by an emitter of the medical device monitoring system, according to an embodiment of the present disclosure.

To further illustrate this, FIG. 3 is a timing diagram or drive control of infrared signals 20a, 20b emitted by emitters 16a, 16b and that includes integral time gaps 26a, 26b. As shown in the illustrated embodiment, the emitter 16a transmits the infrared signal 20a (e.g., a first infrared signal) and the emitter 16b transmits the signal 20b (e.g., a second infrared signal). The infrared signals 20 include time gaps 26 that separate repeats of identification information 24 (e.g., groups of code representative of identification information 24) that is unique to each associated monitor 12. That is, the drive signal may include on periods that represent transmission of the identification information 24 and off periods or dark periods that represent the time gaps 26. The time gaps 26 are variable and, as provided herein, may be set randomly to prevent or reduce simultaneous transmission of identification information 24 between different emitters 16.

As shown in the illustrated example, at a first time point Δt1, the transmission of the identification information 24a occurs simultaneously with the transmission of the identification information 24b. This may lead to the receiver 18 being unable to separate or resolve the simultaneously received identification information 24a, 24b from the emitters 16a, 16b. However, the next on-period for each respective emitter 16a, 16b is staggered or separated in time, because the emitters 16a, 16b independently introduce a random time gap 26 between repeats of the identification information 24. As shown in FIG. 3, the random time gap 26a of the emitter 16a is different than the random time gap 26b introduced by the emitter 16b. During the time gap, the emitters 16a, 16b are off or dark such that no interfering signal is generated. Accordingly, at Δt2, both emitters 16a, 16b are off in accordance with the set random time gap. At Δt3, the random time gap 24a of the emitter 16a has expired, and the emitter 16a transmits the identification information 24a while the emitter 16b is still off. Accordingly, the receiver 18 can resolve the identification information 24a at Δt3 that may not have been resolvable at Δt1 because of interference from the emitter 16b.

Similarly, at Δt4, the identification information 24b is transmitted during an off-period or time gap 26a' of the emitter 16a and is received by the receiver 18 without interference from the emitter 16a. The identification information 24 in each repeat for an individual emitter (e.g., the emitter 16a or the emitter 16b) may be the same between repeats, so that one or two instances of unresolvable identification information 24 will not ultimately prevent efficient pairing. Further, it should be understood that different emitters 16 transmit different identification information 24 relative to each other to permit unique identification of their associated monitors 12.

The random time gap 26 may be set independently at each respective monitor 12. Statistical distribution will govern the likelihood that the random time gaps 26 introduced between repeats 24 for an individual emitter 16 will be sufficiently staggered between two monitors 12. For example, in an embodiment where the time gap 16 for two emitters 16 is generated by selecting a number between 1 and 10 by way of example, the probability that the emitters 16a, 16b will generate the same first time gap is 1/10 and the probability that the emitters 16a, 16b will also have the second time gap is 1/100. The time gap 26 may be based on a random positive number (e.g., from a random number generator with minimum and maximum limits) that is multiplied by a time constant to generate the random time gap 26. As such, an emitter 16 that transmits an infrared signal 20 with a time gap 26 will prevent or reducing overlapping the infrared signal with infrared signals transmitted by other monitors 12. In an embodiment, the system 10 generates a pseudorandom time gap 26. For example, the pseudorandom time gap 26 may be based on a number from a pseudorandom number generator (PRNG). In an embodiment, the system 10 generates the random time gap 26 dynamically in real time. In an embodiment, the system 10 generates the random time gaps 26 as an ordered set in advance or at initiation of transmission by the emitter 16 and applies the ordered set to establish the random time gaps 26 separated by identification information 24 to generate the drive signal for the emitter 16.

In one embodiment, the magnitude (e.g., duration) of the time gap 26 may be based on the signal transfer time 24 of infrared signal 20. For example, the time gap 26a, 26b may be greater than at least twice an estimated or previous (e.g., last) signal transfer time of the identification information 24. In this way, the likelihood of overlap between the infrared signals 20a and 20b may be further reduced as the off-period for the individual infrared signals 20a, 20b is generally longer than the on-period (that includes the identification information 24).

In this manner, multiple emitters 16 emitting in the same waveband may transmit identification information automatically and without having to synchronize the transmissions of the emitters 16 between different monitors 12. Additionally, the receiver 18 may obtain resolvable information from multiple emitters 16, thereby permitting the receiver 18 to pair with one or more emitters 16 automatically.

Figure 4:
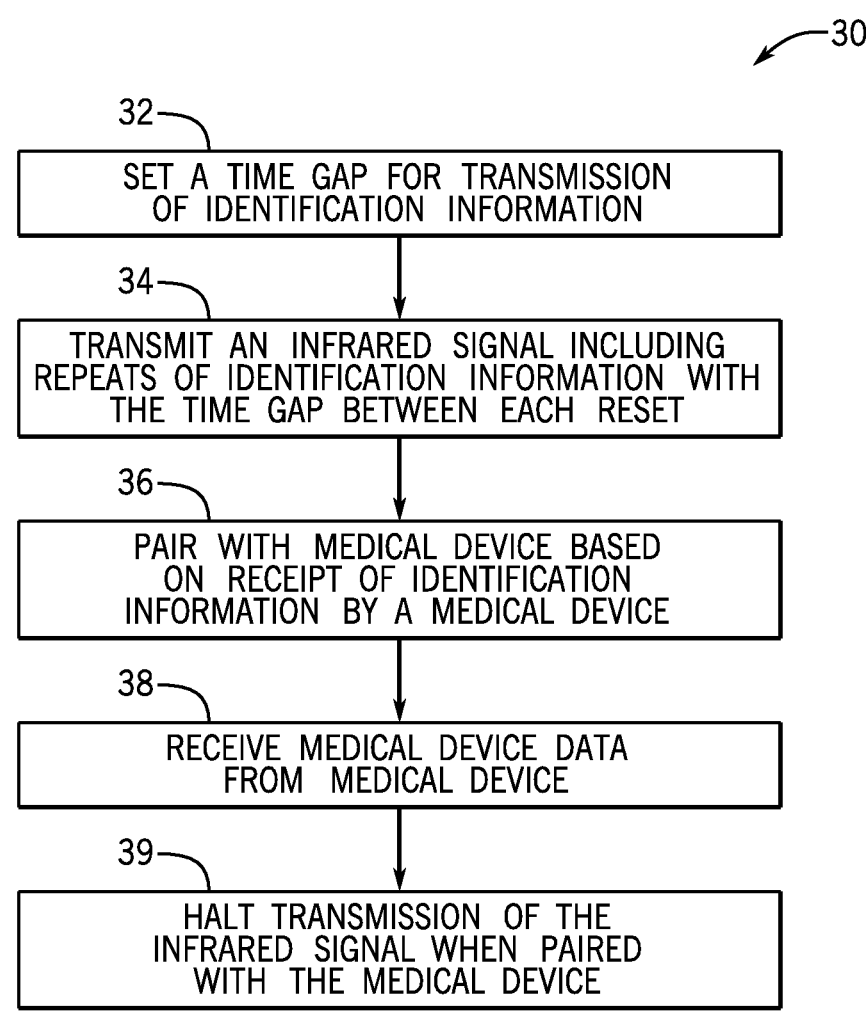
FIG. 4 illustrates a flow diagram for pairing and communicating data between a monitor and a medical device based on infrared signals sent by an emitter, according to an embodiment of the present disclosure.

FIG. 4 illustrates an example process 30 that may be employed by components of the system 10, such as the monitor 12 (e.g., a process of the monitor 12) to pair and communicate with the medical device 14, in accordance with embodiments described herein and with reference to FIGS. 1-3. For example, the steps of the process 30 may be stored in the memory and/or the storage of the monitor 12. Before proceeding, it should be noted that the process 30 described below is described as being performed by the processor of the monitor 12, but the process 30 may be performed by other suitable computing devices. For example, certain steps, such as blocks 32, 34, and 36 may be performed by a processor of the medical device 14 in an embodiment where the medical device 14 includes an emitter (e.g., the infrared emitter 16) and the monitor includes a receiver (e.g., the receiver 18). Although described in a particular order, which represents a particular embodiment, it should be noted that the process 30 may be performed in any suitable order. Additionally, embodiments of the process 30 may omit process blocks and/or include additional process blocks.

Referring now to FIG. 4, at block 32, a processor of the monitor 12, sets a time gap 26, e.g., a random time gap 26, for transmission of identification information 24 of the monitor 12. In general, the identification information is information that may be used by the medical device 14 to pair the monitor 12 and the medical device 14. For example, the identification information may include a MAC address, an IP address, a passkey, and the like, that facilitates pairing between the monitor 12 and the medical device 14. In an embodiment, the processor of the monitor 12 may generate the time gap 26 using a random number generator. For example, the processor of the monitor 12 may randomly generate a number between 0 and 1, a number greater than 1, and/or an integer number using suitable methods, such as pseudorandom number generators (PRNGs) or hardware random-number generators. The time gap 26 may be based on the generated random number multiplied by a time constant. In one embodiment, the monitor 12 may generate the time gap 26 after transmission of a previous infrared signal by the monitor 12. As such, in the event that the previous infrared signal 20 is not resolvable by a receiver 18 of a medical device, the emitter 16 of the monitor 12 may transmit the infrared signal 20 using the time gap 26 to decrease overlap or interference resulting from emitters 16 of other monitors 12 that may have cause the previous infrared signal 20 to be unresolvable by the medical device 14.

In an embodiment where multiple monitors 12 attempt to pair with the medical device 14, if at least one monitor of multiple monitors 12 is generating the time gap using a random number generator (e.g., a random time gap), the likelihood of the infrared signals of each monitor 12 overlapping may decrease, thereby increasing the likelihood that the monitors will pair with one or more medical devices 14. In another embodiment, each monitor of the multiple monitors may generate a respective time gap, which may further decrease the likelihood of the infrared signals of each monitor 12 overlapping.

In another embodiment, the processor of the monitor 12 may generate a time gap 26 based on a signal transfer time associated with the identification information 24. For example, when the identification information 24 is a MAC address, the time gap 26 may correspond to the signal transfer time of sending the complete MAC address via the emitter 16. The signal transfer time may be empirically determined or may be based on a calibration transmission or the last transmission by the emitter 16. To prevent the infrared signal 20 that is transmitted, as discussed with regard to block 34, from overlapping with infrared signals 20 transmitted by additional monitors 12, the time gap 26 may be a multiple of the signal transfer time (e.g., at least twice the signal transfer time, three times the signal transfer time, five times the signal transfer time, and so on). In one embodiment, the time gap 26 may be the signal transfer time combined (e.g., added and/or added) with a random number (e.g., a number between 0 and 1 or a number greater than 1). That is, the processor of the monitor 12 may generate a random positive number and multiply the random positive number by a time constant (e.g., the signal transfer time or other constant) to generate or set the time gap 26. Then, the processor causes the emitter 16 to transmit the infrared signal 20 after the time gap is calculated (e.g., and the time gap has elapsed.) In some embodiments, the processor may generate the time gap 26 and the drive signal of the emitter 16 upon the monitor 12 being powered on.

At block 34, the monitor 12 transmits the infrared signal 20 including the identification information 24 repeated and separated by random time gaps 26. For example, the processor of the monitor 12 may output a control signal that causes the emitter 16 of the monitor 12 to output the infrared signal after the time gap 26. In one embodiment, the processor of the monitor 12 outputs a control signal (e.g., an emitter drive signal) that causes the emitter 16 of the monitor to transmit the infrared signal 20 including the identification information 24 where each repeat is separated by the time gap 26. For example, the processor of the monitor 12 may cause the emitter to repeatedly output the identification information 24 in response to the monitor 12 powering on or after a predetermined delay. When the infrared signal 20 does not overlap or interfere with an infrared signal 20 from an additional monitor 12 to produce an unresolvable signal, the process may proceed to block 36. For example, the monitor 12 may output the infrared signal 20 when the monitor 12 is not paired and until pairing occurs.

At block 36, the monitor 12 pairs with the medical device 14. As discussed herein, pairing refers to establishing a wireless communication, such as between the monitor 12 and the medical device 14. For example, the medical device 14 may receive a resolvable infrared signal from the monitor 12 that includes a unique MAC address associated with the monitor 12. As such, the medical device 14 may identify the monitor 12 on a network communicating with the medical device 14 and the monitor 12. Successful pairing may be indicated by establishing communication via wireless or Bluetooth circuitry and associated handshakes of the monitor 12 and the medical device 14. The medical device 14 may use the unique identification information 24 provided by the monitor 12 to send the appropriate code, key, and/or device identifier to establish the communication with the monitor 12.

In one embodiment, the monitor 12 may deactivate the emitter 16 of the monitor 12 in response to pairing with the medical device. For example, the monitor 12 may output a control signal that causes the emitter 16 to halt transmission of another signal and/or the processor may not generate an additional time gap. In one embodiment, the monitor 12 may return to block 32 when the pairing and/or communication between the monitor 12 and the medical device 14 is interrupted. For example, the monitor 12 may subsequently transmit an additional infrared signal 20 as provided herein. In one embodiment, the processor of the monitor 12 may output a control signal that causes the monitor 12 to display identification information 24 associated with the paired medical device 14 and one or buttons or user inputs that allow the user to confirm whether the monitor 12 is paired with the correct medical device 14. Successful pairing may be indicated by the user input on the monitor 12 and/or the device 14.

At block 38, the monitor 12 receives medical device data from the medical device 14. For example, the monitor 12 may display a stream of medical device data from the medical device 14 in substantially real-time. In some embodiments, the medical device data may include encrypted data. For example, the medical device data may include patient data, medical records, or other data that the medical professional and/or the patient would want secured. As such, the medical device 14 may also transmit an encryption key, thereby permitting the processor of the monitor 12 to decrypt the encrypted data.

Additionally or alternatively, at block 39, the monitor 12 may halt transmission of the infrared signal in response to the monitor 12 pairing with the medical device 14. For example, in response to the establishing communication with the medical device 14, a processor of the monitor 12 may output a control signal that causes the emitter 16 to halt transmission of any additional infrared signals 20 upon indications of successful pairing. In this manner, the monitor 12 pairs to a single medical device 14. The medical device 14 may pair to only a single monitor 12 by automatically deactivating the receiver 18 upon successful pairing. In another embodiment, the medical device 14 may be configured to pair to any available monitor 12, and the receiver 18 is active during the powered-on state of the medical device 14 or until actively turned off by user input. In one embodiment, the monitor 12 may reactivate the emitter 16 when the communication and/or pairing between the monitor 12 and the medical device 14 is interrupted. For example, when the interruption of communication between the monitor 12 and the medical device 14 is greater than a time threshold, the processor of the monitor 12 may output a control signal that reactivates the emitter 16 and the process 30 may return to block 32. The monitor 12 may only activate the emitter 16 when the monitor 12 is not already paired with a medical device 14. In another embodiment where the medical device 14 includes an infrared emitter 16 and the monitor 12 also includes an infrared receiver 18, the emitter 16 may remain active, thereby allowing communication between the medical device 14 and the monitor 12 using an infrared emitter and receiver. For example, the monitor 12 and the medical device 14 may communicate relatively less memory intensive data than video data or imaging data, such as an encryption key.

In this manner, the process 30 may enable the monitor 12 to prevent or reduce overlapping and unresolvable signals, improving pairing between devices, such as the monitor 12 and the medical device. As discussed herein, by transmitting an infrared signal with identification information after a time gap determined by a processor of the monitor 12, the likelihood of the infrared signal overlapping with infrared signals transmitted by other monitors 12 may be reduced.

Figure 5:
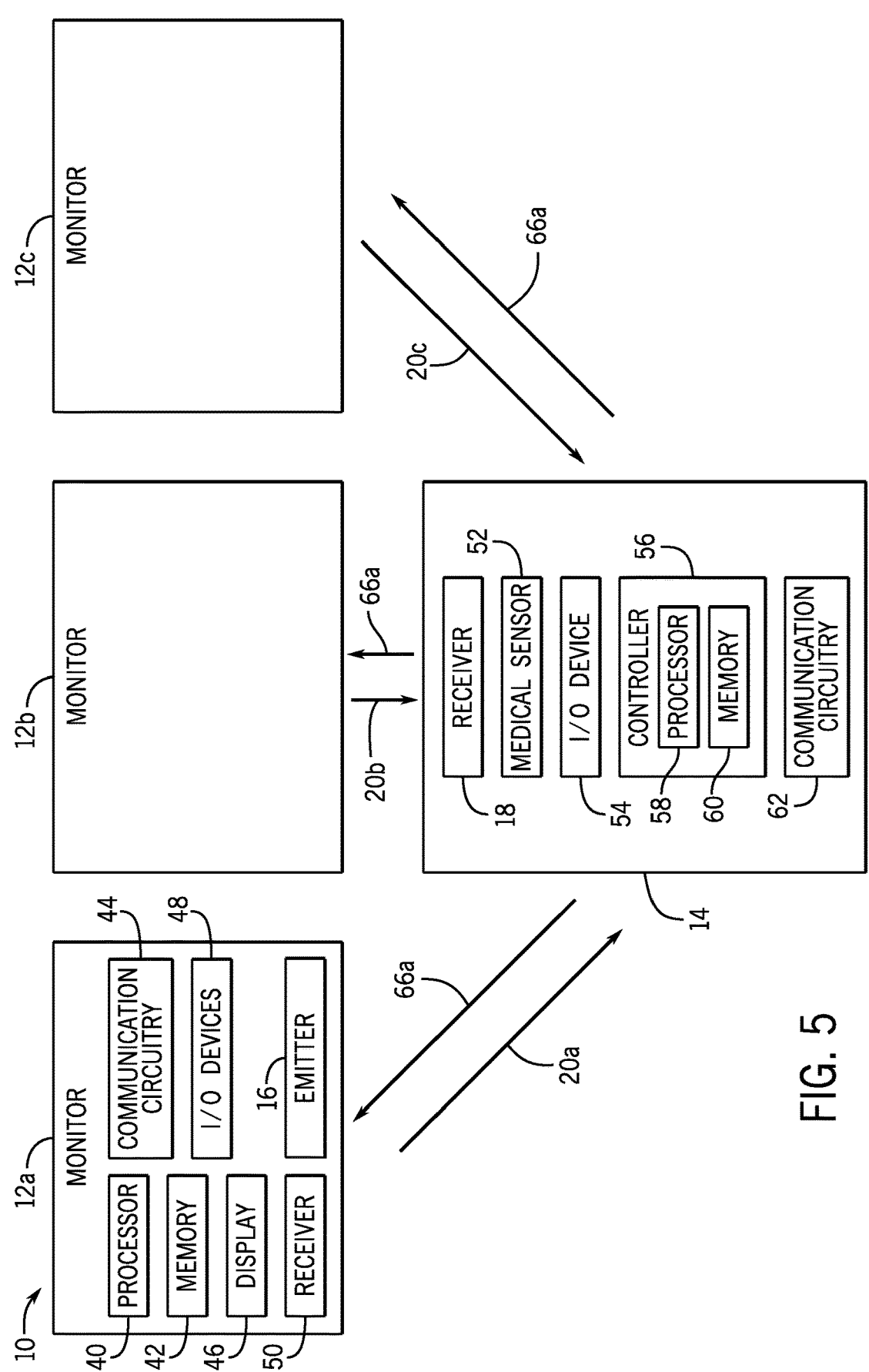
FIG. 5 illustrates a block diagram of monitors and a medical device that may be used in conjunction with the system of FIG. 2, according to an embodiment of the present disclosure.
Figure 6:
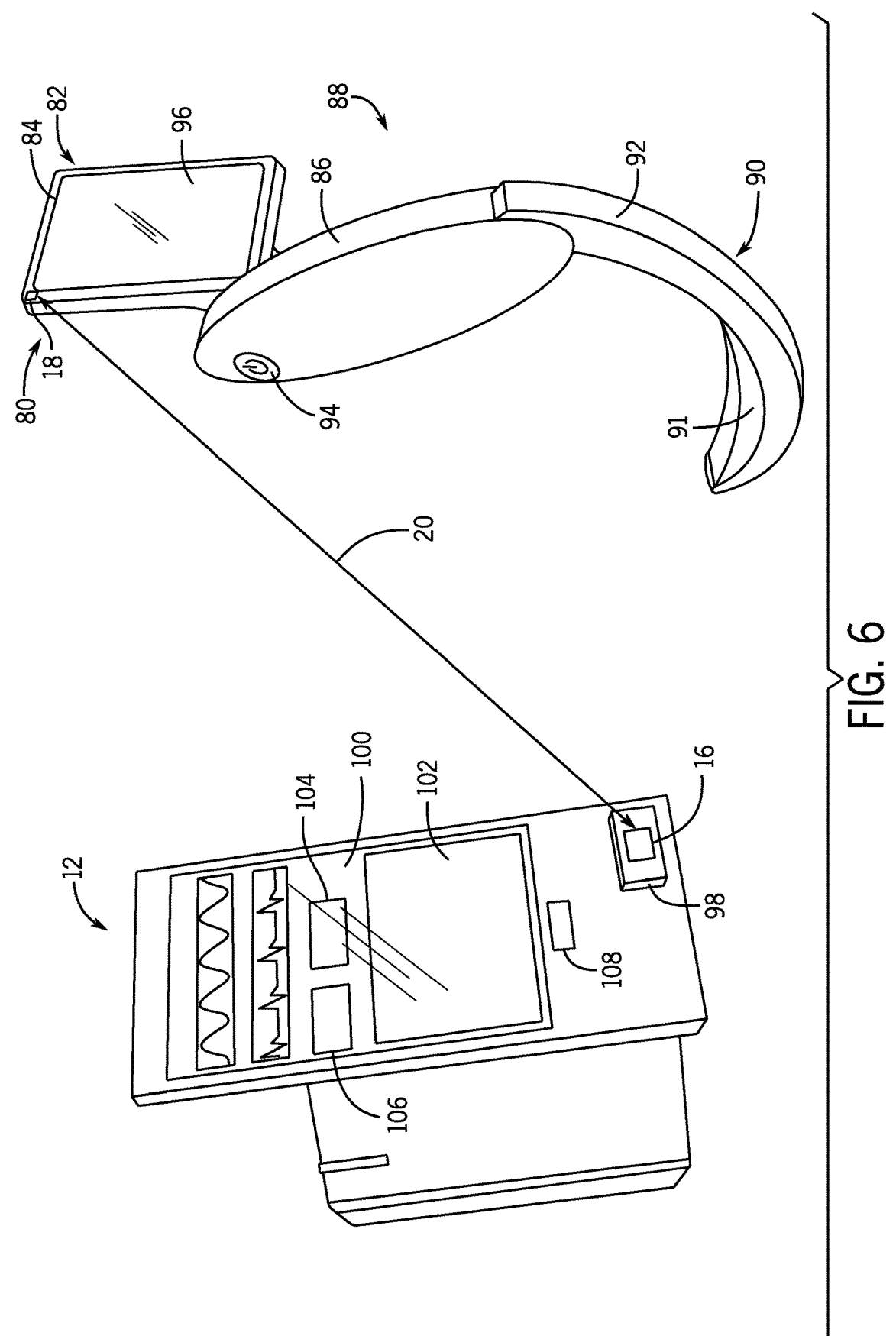
FIG. 6 illustrates a perspective view of a system of video laryngoscope pairing and communicating with a video monitor, according to an embodiment of the present disclosure.

To perform one or more operations described herein, the monitor 12 may include various types of components that may assist the processor of the monitor 12 in performing the operations described below. FIG. 5 is a block diagram of an embodiment of the medical device monitoring system 10. As shown, the medical device monitoring system 10 includes the monitor 12 and the medical device 14 (e.g., a video laryngoscope).

The monitor 12 and the medical device 14 may include various components that enable the medical device monitoring system 10 to carry out the techniques disclosed herein. For example, the monitor 12 includes the emitter 16, one or more processors 40, a hardware memory 42, a communication circuitry 44, a display 46, input/output (I/O) devices 48, and a receiver 50. The monitor 12 may be powered by various power sources, such as a battery or input from an external power source. The medical device 14 may include the receiver 18, a medical sensor (e.g., a camera) 52, I/O devices (e.g., touch sensor) 54, as well as a controller 56 (e.g., electronic controller), one or more processors 58, a hardware memory 60, and communication circuitry 62.

The communication circuitry 44, 62 may be wireless transceivers that are configured to establish wireless communication with one another. By way of example, the communication circuitry 44, 62 may be configured to communicate using the IEEE 802.15.4 standard, and may communicate, for example, using ZigBee, WirelessHART, or MiWi protocols. Additionally or alternatively, the communication circuitry 44, 62 may be configured to communicate using the Bluetooth standard or one or more of the IEEE 802.11 standards. In some embodiments, the communication circuitry 44, 62 may be provided in an adapter (e.g., a dongle) that is configured to couple to the monitor 12 and/or medical device 14 to facilitate wireless communication 66 between the monitor(s) 12 and the medical device 14.

As discussed herein, the medical device 14 may pair and communicate medical device data (e.g., acquired by the medical sensor 52) when the medical device 14 receives a resolvable infrared signal 20. In the illustrated embodiment, each monitor 12a, 12b, and 12c is transmitting a respective infrared signal 20a, 20b, and 20c that may include identification information 24 that is unique to each monitor 12a, 12b, and 12c (e.g., a MAC address of the monitor 12). Moreover, each infrared signal 20a, 20b, and 20c may be transmitted with intervening random time gaps 26 independently set by the processor 40. As such, when the infrared signals 20a, 20b, and 20c are resolvable, the medical device 14 will pair with the monitor 12 that transmitted a resolvable infrared signal 20. In one embodiment, the receiver 18 of the medical device 14 is not inactivated upon pairing with a single monitor 12, and the medical device 14 may be able to pair to each monitor 12a, 12b, and 12c. In this embodiment, the medical device 14 may continuously stream medical device data captured by the medical sensor 52 of the medical device 14. In any case, in response to the medical device 14 receiving a resolvable infrared signal, the medical device 14 communicates with the monitors 12a, 12b, and 12c via a wireless communication 66a, 66b, and/or 66c, respectively.

In certain embodiments, the video laryngoscope monitoring system 10 may include one or more remote devices or systems (not shown), such as computing systems (e.g., handheld or portable computing systems operated by the medical professional, such as a tablet, smart phone, or the like; hospital computing systems; or the like), room display systems, and/or hospital data storage systems. The remote devices or systems may be configured to communicate (e.g., send and/or receive signals from) with the medical device 14 and/or the monitor 12 via wireless or wired connections. For example, the medical device 14 and/or the monitor 12 may relay the image data or sensor data received from the medical device 14 to the remote device or system for display and/or storage.

In certain embodiments, the monitor 12 and the medical device 14 may include electrical circuitry configured to process signals, such as signals generated by the medical sensor 52, and/or control signals provided via inputs, such as the inputs 48 of the monitor 12, or the input 54 on the medical device 14, for example. In the illustrated embodiment, the processors 40, 58 may be used to execute software. For example, in an embodiment where the medical device 14 is a video laryngoscope and the medical sensor 52 includes a camera, the processor 58 of the medical device 14 may be configured to receive signals from the medical sensor 52 and to execute software to generate an image and/or to carry out any of a variety of processes in accordance with the present disclosure (e.g., display the image, store the image, transfer the image, or the like). Moreover, the processors 40, 58 may include multiple microprocessors, one or more "general-purpose" microprocessors, one or more special-purpose microprocessors, and/or one or more application specific integrated circuits (ASICS), or some combination thereof.

For example, the processors 40, 58 may include one or more reduced instruction set (RISC) processors. It should be appreciated that the various processing steps may be carried out by either processor 40, 58 or may be distributed between the processors 40, 58 in any suitable manner.

The hardware memory 42, 60 may include a volatile memory, such as random access memory (RAM), and/or a nonvolatile memory, such as read-only memory (ROM). It should be appreciated that the hardware memory 42, 60 may include flash memory, a hard drive, or any other suitable optical, magnetic, or solid-state storage medium, other hardware memory, or a combination thereof. The memory 42, 60 may store a variety of information and may be used for various purposes. For example, the memory 42, 60 may store processor-executable instructions (e.g., firmware or software) for the processors 40, 58 to execute, such as instructions for generating the time gap 26 and the drive signal of the infrared emitter 16. As discussed herein, the emitter 16 may transmit identification information 24 associated with the monitor 12, such as a MAC address, an IP address, a passkey, and the like. For example, the processor 40 may retrieve the identification information from the memory and/or storage 42 and cause the emitter 16 to emit an infrared signal 20 that includes the identification information 24.

As provided herein, the medical device 14 may be any medical device that is capable of pairing with a separate monitor. In a specific embodiment, the system 10 is a video laryngoscope monitoring system, and the medical device 14 is a video laryngoscope 80. The video laryngoscope 80 including a display portion 82 having a display screen 84 that is configured to display images or other data, and a body 86 (e.g., reusable body) with a handle portion 86 that is configured to be gripped by the medical professional during the laryngoscopy procedure, and an elongate portion or arm 90 that supports a camera assembly 91 that is configured to obtain images (e.g., still images and/or moving images, such as videos). It should be appreciated that the display portion 82 and the handle portion 88 may not be distinct portions, such that the display screen 84 is integrated into the handle portion 88.

The video laryngoscope 80 may also include a power button 94 that enables a medical professional to power the laryngoscope 80 off and on. In one embodiment, the power button 94 may directly control operation of the receiver 18, such that the receiver 18 activates upon powering on of the video laryngoscope 80. In the illustrated embodiment, the video laryngoscope 80 includes an input button, such as a touch or proximity sensor 96 (e.g., capacitive sensor, proximity sensor, or the like) that is configured to detect an object (e.g., a finger or stylus). The touch sensor 96 may enable the medical professional operating the video laryngoscope 80 to efficiently provide inputs or commands, such as inputs that cause the camera (e.g., medical sensor 52) to obtain or store an image on a memory of the laryngoscope and to validate pairing with the monitor 12.

As discussed herein, the monitor 12 includes the emitter 16 that transmits infrared signals 20 that are received by the receiver 18 in range. The video laryngoscope 80 may be configured to communicate with the monitor 12 and/or other remote devices or systems via any of a variety of techniques. For example, as discussed above with respect to FIG. 5, the video laryngoscope 80 and the monitor 12 may include the communication circuitry 44 and 62, respectively, which may be wireless transceivers that are configured to establish wireless communication with one another using any suitable protocol. In certain embodiments, in response to detection of a resolvable infrared signal 20 by the receiver 18, the video laryngoscope 80 automatically transmits data from the storage device of the video laryngoscope 80 to the monitor 12 and/or transmits data to one or more other remote devices or systems at certain times. In the illustrated embodiment, the receiver 18 is disposed on a housing of the display portion 82. However, in one embodiment, the receiver 18 may be disposed on the handle 88.

In the illustrated embodiment, an adapter 98 (e.g., wireless adapter, dongle, or bridge device) is provided to facilitate wireless communication between the video laryngoscope 80 and the monitor 12 and/or other remote devices and systems. That is, the adapter 98 may include the communication circuitry 44 and/or the emitter 16. For example, in the illustrated embodiment, the adapter 98 includes a wireless transceiver that sends information to and receives information from the video laryngoscope 80. The adapter 98 is coupled to the monitor 12 (e.g., by plugging the adapter 98 into a Universal Serial Bus [USB] port of the monitor 12) to relay information or commands between the video laryngoscope 80 and the monitor 12. Such a configuration may enable use of the laryngoscope 80 with third-party monitors or multi-parameter monitors. For example, the adapter 98 may be coupled to a first monitor 12 to enable wireless communication (e.g., transfer of video, image, or device status data between the video laryngoscope 80 and the monitor 12, transfer of an instruction from the monitor 12 to the laryngoscope 80 to obtain a photo using the camera assembly 91, or the like) between the video laryngoscope 80 and the first monitor 12, and the adapter 98 may then be removed from the first monitor 12 and coupled to a second monitor 12 to enable wireless communication between the video laryngoscope 80 and the second monitor 12.

As shown, the monitor 12 includes a display screen 100 (e.g., touchscreen display) that is configured to provide information to the medical professional and/or that is configured to receive inputs. For example, the monitor 12 may provide a still or moving image 102 obtained by the camera assembly 91 of the video laryngoscope 80, and in some cases, may also provide information obtained via various physiological sensors (e.g., heart rate, oxygen saturation, or the like). In some embodiments, the image 102 may be a video that is streamed wirelessly in substantially real-time from the video laryngoscope 80 to the monitor 12. The video laryngoscope 80 and the monitor 12 may interact to carry out various other advanced monitoring functions, such as transfer of data (e.g., images, time data, or the like) from the video laryngoscope 80 to the monitor 12 in response to an input received (e.g., a touch input from the user at the video laryngoscope 80 and/or at the monitor 12) and/or automatic transfer of data from the video laryngoscope 80 to the monitor 12 at certain times (e.g., upon powering the video laryngoscope 80 and/or the monitor off or on, periodically during the laryngoscopy procedure, upon receipt of a user input, upon receipt of an input indicating that the laryngoscopy procedure is complete and/or that certain steps of the laryngoscopy procedure are complete). The monitor 12 may include various other features, such as a power button 108 that enables a user to power the monitor 12 off and on. It should be appreciated that the video laryngoscope 80 and the monitor 12 may also include ports (e.g., USB ports, Ethernet ports, high-definition multimedia interface [HDMI] ports, optical ports, infrared ports, near field ports, or the like) that enable the components to be coupled to one another and/or to other components (e.g., computing systems or storage systems) via a wired connection.

In some embodiments, the display screen 100 of the monitor 12 and/or the display screen 82 of the video laryngoscope 80 may be configured to provide an indication that the monitor 12 and the video laryngoscope 80 are communicatively coupled or paired to one another. In some embodiments, the video laryngoscope 80 may be configured to provide a laryngoscope ID (e.g., numerical or descriptive identifier) to the monitor 12, and the monitor 12 is configured to display the laryngoscope ID on the display screen 100 to enable the medical professional to confirm that the monitor 12 is receiving data from the appropriate video laryngoscope 80. In an embodiment, the monitor 12 is configured to connect to only one video laryngoscope 80 at a time. In another embodiment, the monitor 12 may connect to two or video laryngoscope 80, and the user may select (e.g., by touch input on the display screen 100) the video laryngoscope 80 from which to display images or transfer data. Additionally or alternatively, in some embodiments, the monitor 12 may be configured to provide a monitor ID (e.g., the identification information 24) to the video laryngoscope 80, and the video laryngoscope 80 is configured to display the monitor ID on the display screen 80 to enable the medical professional to confirm that the laryngoscope 80 is transferring data to the appropriate monitor 12. In some embodiments, the monitor 12 and/or the video laryngoscope 80 may enable the medical professional to provide inputs (e.g., via one or more touchscreen display screens 80, 100) to adjust or to select the appropriate device(s) (e.g., the monitor 12 and the video laryngoscope 80) that should communicate with one another during the laryngoscopy procedure. It should be appreciated that the medical professional may provide various inputs disclosed herein via a voice command to a microphone of the video laryngoscope 80. Such configurations may be particularly useful when the video laryngoscope monitoring system 10 is used in an environment or circumstance in which multiple monitors 12 and/or multiple laryngoscopes 14 are operating simultaneously, for example.

FIG. 7 illustrates an example process 110 that may be employed by a monitor 12 (e.g., a process of the monitor 12) to pair and communicate with the video laryngoscope 80, in accordance with embodiments described herein. For example, the steps of the process 110 may be stored in the memory and/or the storage 42. Before proceeding, it should be noted that the process 110 described below is described as being performed by the processor 40 of the monitor 12, but the process 110 may be performed by other suitable computing devices. For example, certain steps, such as blocks 112, 114, and 116 may be performed by a processor 58 of the medical device 14 (i.e., the video laryngoscope 80) in an embodiment where the medical device 14 includes an emitter (e.g., the emitter 16) and the monitor includes a receiver (e.g., the receiver 18). Although described in a particular order, which represents a particular embodiment, it should be noted that the process 110 may be performed in any suitable order. Additionally, embodiments of the process 110 may omit process blocks and/or include additional process blocks.

Referring to now to FIG. 7, at block 112, the processor 40 of the monitor 12 sets a time gap 26 for transmission in a similar manner as described in block 32 of FIG. 4. At block 114, the processor 40 of the monitor 12 transmits the infrared signal including the identification information after the time gap in a similar manner as described in block 34 of FIG. 4. At block 116, the monitor 12 pairs with the video laryngoscope in a similar manner as described in block 36 of FIG. 4

At block 118, the processor 40 of the monitor 12 receives airway images acquired by the video laryngoscope 80 in a similar manner as described in block 38 of FIG. 4 with respect to receiving medical device data. For example, the processor 40 of the monitor 12 may output a control signal that causes the display to stream the airway images on the display 100 of the monitor 12. As discussed herein, the display 100 may include one or more inputs (e.g., inputs 104, 106, and 108) that allow the medical professional to control how the airway images are displayed, such as by taking a screenshot with input 106, changing the image 102 to a display airway images acquired by a different video laryngoscope 80, and so on. At block 120, the processor 40 of the monitor 12 halts transmission of the infrared signal by the emitter 16 in a similar manner as described in block 39 of FIG. 4.

In this manner, the process 110 may enable the monitor 12 to prevent or reduce overlapping and unresolvable signals, improving pairing between devices, such as the monitor 12 and the video laryngoscope 80. As discussed herein, by transmitting an infrared signal with identification information after a time gap determined by a processor of the monitor 12, the likelihood of the infrared signal overlapping with infrared signals transmitted by other monitors 12 may be reduced.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A video laryngoscope monitoring system, comprising:
   a monitor comprising:
      an infrared emitter that is activated to emit:
         an infrared signal, the infrared signal comprising a first signal portion comprising identification information of the monitor and a second signal portion comprising the identification information, wherein there is a random time gap, the random time gap based on a random number or a pseudorandom number, between the first signal portion and the second signal portion;
      a controller that activates the infrared emitter and that sets the random time gap between the first signal portion and the second signal portion; and
      monitor communication circuitry; and
   a video laryngoscope comprising:
      a camera that acquires airway images of a patient;
      an infrared receiver disposed on the video laryngoscope and that receives the infrared signal from the infrared emitter comprising the identification information of the monitor;
      communication circuitry that wirelessly communicates with the monitor communication circuitry; and
      a processor that:
         extracts the identification information from the infrared signal;
         validates a pairing between the video laryngoscope and the monitor based on the extracted identification information; and
         instructs the communication circuitry to wirelessly communicate the acquired airway images to the monitor associated with the identification information based on the validated pairing.

2. The video laryngoscope monitoring system of claim 1, wherein the controller deactivates the infrared emitter upon the monitor communication circuitry receiving the acquired airway images.

3. The video laryngoscope monitoring system of claim 2, wherein the controller reactivates the infrared emitter when the monitor communication circuitry is not receiving the acquired airway images.

4. The video laryngoscope monitoring system of claim 1, wherein the processor activates the infrared receiver upon the video laryngoscope powering on.

5. The video laryngoscope monitoring system of claim 1, wherein the infrared emitter does not emit infrared light during the random time gap such that the first signal portion and the second signal portion of the infrared signal are separated by a dark period.

6. The video laryngoscope monitoring system of claim 1, wherein the processor deactivates the infrared receiver upon the communication circuitry communicating the acquired airways to the monitor communication circuitry.

7. The video laryngoscope monitoring system of claim 6, wherein the processor reactivates the infrared receiver when the communication circuitry is not communicating the acquired airway images.

8. The video laryngoscope monitoring system of claim 1, wherein the infrared receiver receives a second infrared signal, the second infrared signal comprising signal portions comprising second identification information separated by a second random time gap that is different than the random time gap and wherein the processor of the video laryngoscope extracts the second identification information from the second infrared signal.

9. The video laryngoscope monitoring system of claim 1, wherein the infrared signal comprises a third signal portion comprising the identification information, wherein the second signal portion and the third signal portion are separated by a second random time gap different than the random time gap.

10. The video laryngoscope monitoring system of claim 1, wherein the identification information comprises a unique identifier of the monitor that is used to establish wireless communication via the communication circuitry of the video laryngoscope.

11. The video laryngoscope monitoring system of claim 1, wherein the monitor comprises an adapter removably coupled to an input port of the monitor, and wherein the adapter comprises the infrared emitter.

12. The video laryngoscope monitoring system of claim 1, wherein the monitor comprises a display that displays the acquired airway images.

13. The video laryngoscope monitoring system of claim 1, wherein the video laryngoscope comprises a display that displays the extracted identification information, and wherein the processor receives a user input on the display selecting the displayed extracted identification information to validate the pairing.

14. The video laryngoscope monitoring system of claim 1, wherein the infrared receiver is disposed on an exterior surface of a body or a display housing of the video laryngoscope.

15. A medical device monitoring system, comprising:
a plurality of monitors, wherein each monitor of the plurality of monitors comprises:
an infrared emitter that is activated to emit an infrared signal comprising identification information of a respective monitor, the identification information repeated in the infrared signal with a random time gap between repeats;
a controller that activates the infrared emitter and that sets the random time gap in the infrared signal of the respective monitor; and
monitor communication circuitry; and
a medical device comprising:
a sensor that acquires medical device data of a patient;
an infrared receiver disposed on the medical device and that receives the infrared signal comprising the identification information from each monitor of the plurality of monitors in accordance with the random time gap of each infrared emitter;
a processor that extracts the identification information from the infrared signal of each monitor; and
communication circuitry that communicates the medical device data to the monitor communication circuitry of at least one monitor of the plurality of monitors using the identification information of the at least one monitor extracted from the infrared signal.

16. The medical device monitoring system of claim 15, wherein the random time gap of the respective monitor is set to be greater than twice a signal transfer time of the identification information of the respective monitor.

17. The medical device monitoring system of claim 15, wherein the identification information of each respective monitor comprises a media access control (MAC) address.

18. The medical device monitoring system of claim 15, wherein at least one monitor of the plurality of monitors further comprises:
an additional infrared receiver that receives the medical device data from an additional infrared emitter of the medical device.

19. A method performed by a monitor, the method comprising:
setting a random time gap based on a signal transfer time of identification information associated with the monitor;
driving transmission of an infrared signal by an infrared emitter, the infrared signal comprising repeats of the identification information, wherein at least two of the repeats are separated by a signal off period having a length based on the random time gap;
pairing with a medical device based on receipt of the infrared signal by an infrared receiver of the medical device, wherein the pairing comprises extracting the identification information from the infrared signal and validating the identification information; and
receiving medical device data from the medical device based on the pairing.

20. The method of claim 19, comprising halting transmission of the infrared signal upon pairing with the medical device.

* * * * *